(12) United States Patent
Suwa

(10) Patent No.: US 8,648,101 B2
(45) Date of Patent: Feb. 11, 2014

(54) NEMATICIDAL AGENT COMPOSITION AND METHOD OF USING THE SAME

(75) Inventor: Akiyuki Suwa, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 457 days.

(21) Appl. No.: 12/593,436

(22) PCT Filed: Apr. 11, 2008

(86) PCT No.: PCT/JP2008/057208
§ 371 (c)(1),
(2), (4) Date: Sep. 28, 2009

(87) PCT Pub. No.: WO2008/126922
PCT Pub. Date: Oct. 23, 2008

(65) Prior Publication Data
US 2010/0048647 A1 Feb. 25, 2010

(30) Foreign Application Priority Data

Apr. 12, 2007 (JP) ................................. 2007-104494

(51) Int. Cl.
*A01N 43/40* (2006.01)
*A61K 31/44* (2006.01)
*C07D 213/56* (2006.01)

(52) U.S. Cl.
USPC ............................ 514/357; 546/336; 546/337

(58) Field of Classification Search
USPC .................................... 514/357; 546/336, 337
See application file for complete search history.

(56) References Cited

U.S. PATENT DOCUMENTS

| | | |
|---|---|---|
| 2003/0162812 A1 | 8/2003 | Harmsen et al. |
| 2010/0249193 A1 | 9/2010 | Andersch et al. |

FOREIGN PATENT DOCUMENTS

| | | |
|---|---|---|
| EP | 1 997 800 A1 | 12/2008 |
| EP | 2 039 772 A2 | 3/2009 |
| JP | 07-010841 A | 1/1995 |
| JP | 2001-342183 A | 12/2001 |
| JP | 2002-532497 A | 10/2002 |
| WO | WO 2004/016088 A2 | 2/2004 |
| WO | WO 2004/074280 A1 | 9/2004 |
| WO | WO 2007/108483 A1 | 9/2007 |
| WO | WO 2010/108616 A1 | 9/2010 |
| WO | WO 2012/038476 A1 | 3/2012 |

OTHER PUBLICATIONS (http://www.soilhealth.see.uwa.edu.au/management/disease, 2004).*
Gowen, "Chemical Control of Nematodes: Efficiency and Side-Effects" in *Plant Nematode Problems and their Control in the Near East Region, FAO Plant Production and Protection Paper—144* (Maqbool et al., eds., Food and Agriculture Association of the United Nations, Rome, Italy, 1997).
*The Merck Index*, 12th Edition (Budavari et al., eds.), pp. 42, 267, 294, 359, 360, 480, 520, 639, 646, 671, 679, 875, 1031, 1039, 1187, 1564, 1565, and 1594 (Merck & Co., Inc., Whitehouse Station, New Jersey, USA, 1996).
*The Pesticide Manual*, 8th Edition (Worthing et al., eds.), pp. 9, 187, and 540 (British Crop Protection Council, Croydon, England, 1987).
Japanese Patent Office, International Search Report in International Patent Application No. PCT/JP2008/057208 (May 13, 2008) English.
European Patent Application, Extended European Search Report in European Patent Application No. 08740305.1 (May 3, 2012).

* cited by examiner

*Primary Examiner* — Sreeni Padmanabhan
*Assistant Examiner* — Uma Ramachandran
(74) *Attorney, Agent, or Firm* — Leydig, Voit & Mayer, Ltd.

(57) ABSTRACT

The present invention provides a nematocide containing, as an active ingredient, an N-2-(pyridyl)ethylcarboxamide derivative represented by the formula (I):

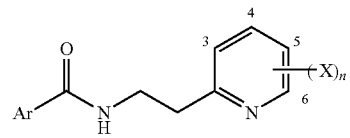

wherein Ar is a substituted phenyl group having one or more, the same or different substituents selected from a halogen atom, a ($C_1$-$C_6$)alkyl group, a halo($C_1$-$C_6$)alkyl group, a ($C_1$-$C_6$)alkylthio group, a halo($C_1$-$C_6$)alkylthio group, a ($C_1$-$C_6$) alkoxy group and a halo($C_1$-$C_6$)alkoxy group, and the like, X may be the same or different, and is a hydrogen atom, a halogen atom, a ($C_1$-$C_6$)alkyl group, a halo($C_1$-$C_6$)alkyl group, and the like, and n is the integer 0 to 4, or a salt thereof, and a method of controlling nematodes, including applying the above compound. The present invention can provide a nematocide or a method of controlling nematodes that exerts a reduced impact on the global environment, exhibits a broad nematode control spectrum at low application rates, and has an excellent nematode control effect.

3 Claims, No Drawings

NEMATICIDAL AGENT COMPOSITION AND METHOD OF USING THE SAME

TECHNICAL FIELD

The present invention relates to a nematocide comprising a known N-2-(pyridyl)ethylcarboxamide derivative as an active ingredient and a method of using the same.

BACKGROUND OF THE INVENTION

Conventionally, it is known that N-2-(pyridyl)ethylcarboxamide derivatives are useful as plant disease control agents (see, for example, Patent Document 1 or 2). However, these prior art documents do not state or suggest that N-2-(pyridyl)ethylcarboxamide derivatives possess nematocidal activity.
Patent Document 1: WO2004/016088
Patent Document 2: WO2004/074280

DISCLOSURE OF THE INVENTION

Problems to be Solved by the Invention

In crop production in agriculture, horticulture and the like, damage by nematodes is still great; there is a demand for the development of a novel nematocide that exhibits a broad nematode control spectrum at low application rates as a solution to problems such as the onset of resistance to existing agents and impact on the global environment. Additionally, aging of farmers and other factors have led to a need for various methods of application with reduced labor, and there is a demand for the creation of a nematocide that befits such methods of application. Aiming at meeting these demands, the present invention provides a nematocide comprising an N-2-(pyridyl)ethylcarboxamide derivative or a salt thereof as an active ingredient.

Means of Solving the Problems

The present inventors conducted extensive investigations to solve the above-described problems, and found that an N-2-(pyridyl)ethylcarboxamide derivative, which is a known compound represented by the formula (I), or a salt thereof exhibits excellent performance for a nematocide, which resulted in completing the present invention. Accordingly, the present invention relates to:

[1] a nematocide comprising, as an active ingredient, an N-2-(pyridyl)ethylcarboxamide derivative represented by the formula (I):

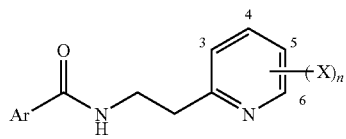

the formula (I)

wherein,
Ar is a substituted phenyl group having one or more, the same or different substituents selected from a halogen atom, a $(C_1-C_6)$alkyl group, a halo$(C_1-C_6)$alkyl group, a $(C_1-C_6)$alkylthio group, a halo$(C_1-C_6)$alkylthio group, a $(C_1-C_6)$alkoxy group and a halo$(C_1-C_6)$alkoxy group; a substituted pyridyl group having one or more, the same or different substituents selected from a halogen atom, a $(C_1-C_6)$alkyl group, a halo$(C_1-C_6)$alkyl group, a $(C_1-C_6)$alkylthio group, a halo $(C_1-C_6)$alkylthio group, a $(C_1-C_6)$alkoxy group and a halo$(C_1-C_6)$alkoxy group; a substituted pyrazinyl group having one or more, the same or different substituents selected from a halogen atom, a $(C_1-C_6)$alkyl group, a halo$(C_1-C_6)$alkyl group, a $(C_1-C_6)$alkylthio group, a halo$(C_1-C_6)$alkylthio group, a $(C_1-C_6)$alkoxy group and a halo$(C_1-C_6)$alkoxy group; or a substituted pyrazolyl group having one or more, the same or different substituents selected from a halogen atom, a $(C_1-C_6)$alkyl group, a halo$(C_1-C_6)$alkyl group, a $(C_1-C_6)$alkylthio group, a halo$(C_1-C_6)$alkylthio group, a $(C_1-C_6)$alkoxy group and a halo $(C_1-C_6)$alkoxy group;
X may be the same or different, and is a halogen atom, a $(C_1-C_6)$alkyl group, a halo$(C_1-C_6)$alkyl group, a $(C_1-C_6)$alkoxy group or a halo$(C_1-C_6)$alkoxy group, and
n is the integer 0 to 4, or a salt thereof,

[2] the nematocide of [1], wherein Ar is a substituted phenyl group having one or more, the same or different substituents selected from a halogen atom, a $(C_1-C_6)$alkyl group, a halo$(C_1-C_6)$alkyl group and a $(C_1-C_6)$alkylthio group; a substituted pyridyl group having one or more, the same or different substituents selected from a halogen atom and a halo$(C_1-C_6)$alkyl group; a substituted pyrazinyl group having one or more, the same or different substituents selected from a halo$(C_1-C_6)$ alkyl group; or a substituted pyrazolyl group having one or more, the same or different substituents selected from a halogen atom and a $(C_1-C_6)$alkyl group; X may be the same or different, and is a halogen atom or a halo$(C_1-C_6)$alkyl group;
and n is the integer 0 to 3,

[3] the nematocide of [1], wherein the nematocide comprises an N-[2-(3-chloro-5-trifluoromethylpyridin-2-yl)ethyl]-2-trifluoromethylbenzamide or a salt thereof as an active ingredient,

[4] a method of controlling nematodes, comprising applying an effective amount of an N-2-(pyridyl)ethylcarboxamide derivative represented by the formula (I):

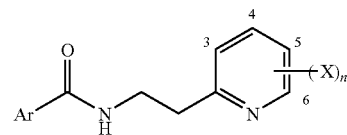

wherein,
Ar is a substituted phenyl group having one or more, the same or different substituents selected from a halogen atom, a $(C_1-C_6)$alkyl group, a halo$(C_1-C_6)$alkyl group, a $(C_1-C_6)$ alkylthio group, a halo$(C_1-C_6)$alkylthio group, a $(C_1-C_6)$ alkoxy group and a halo$(C_1-C_6)$alkoxy group; a substituted pyridyl group having one or more, the same or different substituents selected from a halogen atom, a $(C_1-C_6)$alkyl group, a halo$(C_1-C_6)$alkyl group, a $(C_1-C_6)$alkylthio group, a halo $(C_1-C_6)$alkylthio group, a $(C_1-C_6)$alkoxy group and a halo$(C_1-C_6)$alkoxy group; a substituted pyrazinyl group having one or more, the same or different substituents selected from a halogen atom, a $(C_1-C_6)$alkyl group, a halo$(C_1-C_6)$alkyl group, a $(C_1-C_6)$alkylthio group, a halo $(C_1-C_6)$alkylthio group, a $(C_1-C_6)$alkoxy group and a halo$(C_1-C_6)$alkoxy group; or a substituted pyrazolyl group having one or more, the same or different substituents selected from a halogen atom, a $(C_1-C_6)$alkyl group, a halo$(C_1-C_6)$alkyl group, a $(C_1-C_6)$alkylthio group, a halo (C$_1$-C$_6$)alkylthio group, a (C$_1$-C$_6$)alkoxy group and a halo(C$_1$-C$_6$)alkoxy group;

X may be the same or different, and is a halogen atom, a (C$_1$-C$_6$)alkyl group, a halo(C$_1$-C$_6$)alkyl group, a (C$_1$-C$_6$) alkoxy group or a halo(C$_1$-C$_6$)alkoxy group, and n is the integer 0 to 4, or a salt thereof to a subject crop plant, subject crop plant seeds, or soil used to cultivate the plant, and

[5] a use as a nematocide of an N-2-(pyridyl)ethylcarboxamide derivative represented by the formula (I):

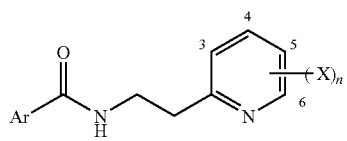

wherein,

Ar is a substituted phenyl group having one or more, the same or different substituents selected from a halogen atom, a (C$_1$-C$_6$)alkyl group, a halo(C$_1$-C$_6$)alkyl group, a (C$_1$-C$_6$) alkylthio group, a halo (C$_1$-C$_6$)alkylthio group, a (C$_1$-C$_6$) alkoxy group and a halo(C$_1$-C$_6$)alkoxy group; a substituted pyridyl group having one or more, the same or different substituents selected from a halogen atom, a (C$_1$-C$_6$)alkyl group, a halo(C$_1$-C$_6$)alkyl group, a (C$_1$-C$_6$)alkylthio group, a halo (C$_1$-C$_6$)alkylthio group, a (C$_1$-C$_6$)alkoxy group and a halo(C$_1$-C$_6$)alkoxy group; a substituted pyrazinyl group having one or more, the same or different substituents selected from a halogen atom, a (C$_1$-C$_6$)alkyl group, a halo(C$_1$-C$_6$)alkyl group, a (C$_1$-C$_6$)alkylthio group, a halo(C$_1$-C$_6$)alkylthio group, a (C$_1$-C$_6$)alkoxy group and a halo(C$_1$-C$_6$)alkoxy group; or a substituted pyrazolyl group having one or more, the same or different substituents selected from a halogen atom, a (C$_1$-C$_6$)alkyl group, a halo(C$_1$-C$_6$)alkyl group, a (C$_1$-C$_6$)alkylthio group, a halo (C$_1$-C$_6$)alkylthio group, a (C$_1$-C$_6$)alkoxy group and a halo(C$_1$-C$_6$)alkoxy group;

X may be the same or different, and is a halogen atom, a (C$_1$-C$_6$)alkyl group, a halo(C$_1$-C$_6$)alkyl group, a (C$_1$-C$_6$) alkoxy group or a halo(C$_1$-C$_6$)alkoxy group, and n is the integer 0 to 4, or a salt thereof.

Effect of the Invention

According to the present invention, it is possible to provide a nematocide that exerts a reduced impact on the global environment, exhibits a broad nematode control spectrum at low application rates, and has an excellent nematode control effect.

BEST MODE FOR CARRYING OUT THE INVENTION

The definitions of the formula (I) for an N-2-(pyridyl) ethylcarboxamide derivative of the present invention are described below.

"A halogen atom" refers to a chlorine atom, bromine atom, iodine atom or fluorine atom.

"A (C$_1$-C$_6$)alkyl group" refers to, for example, a linear or branched alkyl group having 1 to 6 carbon atoms, such as a methyl group, ethyl group, normal propyl group, isopropyl group, normal butyl group, isobutyl group, secondary butyl group, tertiary butyl group, normal pentyl group, neopentyl group, or normal hexyl group.

"A halo(C$_1$-C$_6$)alkyl group" refers to, for example, a linear or branched alkyl group having 1 to 6 carbon atoms, substituted by one or more, the same or different halogen atoms such as a trifluoromethyl group, difluoromethyl group, perfluoroethyl group, perfluoroisopropyl group, chloromethyl group, bromomethyl group, 1-bromoethyl group, or 2,3-dibromopropyl group.

"A (C$_1$-C$_6$)alkoxy group" refers to, for example, a linear or branched alkoxy group having 1 to 6 carbon atoms, such as a methoxy group, ethoxy group, normal propoxy group, isopropoxy group, normal butoxy group, secondary butoxy group, tertiary butoxy group, normal pentyloxy group, isopentyloxy group, neopentyloxy group, or normal hexyloxy group.

"A halo(C$_1$-C$_6$)alkoxy group" refers to, for example, a linear or branched alkoxy group having 1 to 6 carbon atoms substituted by one or more, the same or different halogen atoms such as a trifluoromethoxy group, difluoromethoxy group, perfluoroethoxy group, perfluoroisopropoxy group, chloromethoxy group, bromomethoxy group, 1-bromoethoxy group, or 2,3-dibromopropoxy group.

"A (C$_1$-C$_6$)alkylthio group" refers to, for example, a linear or branched alkylthio group having 1 to 6 carbon atoms such as a methylthio group, ethylthio group, normal propylthio group, isopropylthio group, normal butylthio group, secondary butylthio group, tertiary butylthio group, normal pentylthio group, isopentylthio group, or normal hexylthio group.

"A halo (C$_1$-C$_6$)alkylthio group" refers to a linear or branched alkylthio group having 1 to 6 carbon atoms, substituted by one or more, the same or different halogen atoms for example, a trifluoromethylthio group, difluoromethylthio group, perfluoroethylthio group, perfluoroisopropylthio group, chloromethylthio group, bromomethylthio group, 1-bromoethylthio group, 2,3-dibromopropylthio group or the like.

Examples of salts of an N-2-(pyridyl)ethylcarboxamide derivative of the present invention, represented by the formula (I), include inorganic acid salts such as hydrochloride, sulfate, nitrate, or phosphate; organic acid salts such as acetate, fumarate, maleate, oxalate, methanesulfonate, benzenesulfonate, or para-toluenesulfonate; and salts with inorganic or organic bases such as sodium ion, potassium ion, calcium ion, or trimethylammonium.

In an N-2-(pyridyl)ethylcarboxamide derivative of the present invention, represented by the formula (I), Ar is preferably a substituted phenyl group having one or more, the same or different substituents selected from a halogen atom, a (C$_1$-C$_6$)alkyl group, a halo (C$_1$-C$_6$)alkyl group and a (C$_1$-C$_6$)alkylthio group; a substituted pyridyl group having one or more, the same or different substituents selected from a halogen atom and a halo(C$_1$-C$_6$)alkyl group; a substituted pyrazinyl group having one or more, the same or different substituents selected from a halo(C$_1$-C$_6$)alkyl group; or a substituted pyrazolyl group having one or more, the same or different substituents selected from a halogen atom and a (C$_1$-C$_6$)alkyl group; and Ar is particularly preferably a 2-trifluoromethylphenyl group. The substitution position for X is not particularly limited, as far as it is substitutable on the pyridine ring of the formula (I); preferably, the substitution position is the 3-position and 5-position on the pyridine ring of the formula (I). X, whether the same or different, is preferably a halogen atom or a halo(C$_1$-C$_6$)alkyl group, particularly preferably one wherein a chloro group is present at the 3-position on the pyridine ring of the formula (I), and a trifluoromethyl group is present at the 5-position. Preferably, n is the integer 0 to 3, particularly preferably 2.

An N-2-(pyridyl)ethylcarboxamide derivative of the present invention, represented by the formula (I), is a known compound, and can be produced according to a method described in a known reference document (see, for example, the aforementioned Patent Document 1 or 2). Specific examples of such compounds are given in Table 1, to which, however, the present invention is not limited. In Table 1, "Ph" represents a phenyl group, and "A1" to "A4" represent the following groups.

TABLE 1

A1: 2-chloropyridin-3-yl

A2: 4-(trifluoromethyl)pyridin-3-yl

A3: 3-(trifluoromethyl)pyrazin-2-yl

A4: 4-chloro-3-ethyl-1-methyl-1H-pyrazol-5-yl

Formula (I)

$$Ar-C(=O)-NH-CH_2CH_2-\text{pyridyl}(X)_n$$

| compound No. | Ar | X | melting point |
|---|---|---|---|
| 1 | 2-Cl—Ph | 3-Cl-5-CF$_3$ | 95-96° C. |
| 2 | 2-Br—Ph | 3-Cl-5-CF$_3$ | 104-106° C. |
| 3 | 2-I—Ph | 3-Cl-5-CF$_3$ | 128-129° C. |
| 4 | 2-CH$_3$—Ph | 3-Cl-5-CF$_3$ | 107-109° C. |
| 5 | 2-CF$_3$—Ph | H | 112-113° C. |
| 6 | 2-CF$_3$—Ph | 5-CF$_3$ | 91-92° C. |
| 7 | 2-CF$_3$—Ph | 3-Cl-5-CF$_3$ | 106-111° C. |
| 8 | 2-CH$_3$S—Ph | 3-Cl-5-CF$_3$ | 89-90° C. |
| 9 | 4-CF$_3$—Ph | 3-Cl-5-CF$_3$ | 151-152° C. |
| 10 | 2,6-F$_2$—Ph | 3-Cl-5-CF$_3$ | 98-99° C. |
| 11 | 2,6-Cl$_2$—Ph | 3-Cl-5-CF$_3$ | 110-111° C. |
| 12 | A1 | 3-Cl-5-CF$_3$ | 105-106° C. |
| 13 | A2 | 3-Cl-5-CF$_3$ | 140-141° C. |
| 14 | A3 | 3-Cl-5-CF$_3$ | 130-131° C. |
| 15 | A4 | 3-Cl-5-CF$_3$ | 97-98° C. |

Nematocides comprising as an active ingredient an N-2-(substituted pyrazolyl)ethylcarboxamide derivative of the present invention, represented by the formula (I), or a salt thereof, are suitable for the control of nematodes in soil in the fields of fruit trees, vegetables, other crops and ornamental plants.

Examples of nematodes to which a nematocide of the present invention is applicable include, but are not limited to, nematodes of the genus *Meloidogyne* such as the southern root-knot nematode (*Meloidogyne incognita*), Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylelenchus destructor*) and bulb and stem nematode (*Ditylelenchus dipsaci*); nematodes of the genus *Pratylenchus* such as the cobb root-lesion nematode (*Pratylenchus penetrans*), chrysanthemum root-lesion nematode (*Pratylenchus fallax*), coffee root-lesion nematode (*Pratylenchus coffeae*), tea root-lesion nematode (*Pratylenchus loosi*), and walnut root-lesion nematode (*Pratylenchus vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera shachtoii*); nematodes of the genus *Aphelenchoides* such as the rice white-tip nematode (*Aphelenchoides besseyi*), chrysanthemum foliar nematode (*Aphelenchoides ritzemabosi*), and strawberry nematode (*Aphelenchoides fragarieae*); nematodes of the genus *Aphelenchus* such as the mycophagous nematode (*Aphelenchus avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like. Furthermore, a nematocidal composition of the present invention is also effective against animal parasitic nematodes such as ascarid, oxyurid, *anisakis*, filaria, *Wuchereria bancrofti*, *Onchocerca volvulus*, and *Gnathostoma*.

Plants for which a nematocide of the present invention can be used are not particularly limited; for example, plants such as cereals (for example, rice, barley, wheat, rye, oat, corn, kaoliang and the like), beans (soybean, azuki bean, broad bean, peas, peanuts and the like), fruit trees/fruits (apples, citruses, pears, grapes, peaches, Japanese apricots, cherries, walnuts, almonds, bananas, strawberries and the like), vegetables (cabbage, tomato, spinach, broccoli, lettuce, onion, Welsh onion, green pepper and the like), root crops (carrot, potato, sweet potato, radish, lotus root, turnip and the like), industrial crops (cotton, hemp, paper mulberry, mitsumata, rape, beet, hop, sugarcane, sugar beet, olive, rubber, coffee, tobacco, tea and the like), pepos (pumpkin, cucumber, watermelon, melon and the like), pasture plants (orchardgrass, sorghum, thimosy, clover, alfalfa and the like), lawngrasses (mascarene grass, bentgrass and the like), crops for flavorings etc. (lavender, rosemary, thyme, parsley, pepper, ginger and the like), and flower plants (chrysanthemum, rose, orchids and the like) can be mentioned.

In recent years, there have been advances in IPM (integrated pest management) technologies using genetically modified crops (herbicide-resistant crops, insect pest-resistant crops incorporating an insecticidal protein production gene, disease-resistant crops incorporating a disease resistance inducing substance production gene, crops with improved palatability, crops with improved storage stability, crops with improved yields, and the like), insect pheromones (tortricid and noctuid mating disrupters and the like), natural enemy insects and the like; a nematocide of the present invention can be used in combination or systematization with these technologies.

Although the active ingredient N-2-(pyridyl)ethylcarboxamide derivative or salt thereof, represented by the formula (I), can be used as it is, without adding other ingredients, it is normally preferable that the active ingredient be used after being prepared as a formulation with a convenient form by a conventional method of agricultural chemical making.

Specifically, an N-2-(pyridyl)ethylcarboxamide derivative represented by the formula (I) or a salt thereof may be blended in an appropriate inert carrier, along with an auxiliary agent added as necessary, in an appropriate ratio, and dissolved, separated, suspended, mixed, impregnated, adsorbed or sticked to obtain an appropriate formulation, for example, a suspension, emulsion, solution, wettable powder, water dispersible granule, granules, dust, tablets, packs and the like.

Any inert carrier can be used in the present invention, whether solid or liquid; as examples of materials that can serve as solid carrier, soybean flour, cereal flour, wood flour, bark flour, sawing dust, powdered tobacco stalks, powdered walnut shells, bran, powdered cellulose, plant extract extraction residues, synthetic polymers such as milled synthetic resins, inorganic mineral powders such as clays (for example, kaolin, bentonite, acid clay and the like), talcs (for example, talc, pyrophyllite and the like), silicas {for example, diatomaceous earth, siliceous sand, mica, white carbons (synthetic highly-dispersed silicic acids also known as hydrated micropowder silicon and silicic hydrate; some products contain calcium silicate as a main ingredient.)}, activated charcoal, sulfur powder, pumice, burnt diatomaceous earth, pulverized bricks, fly ash, sand, calcium carbonate, and calcium phosphate, plastic carriers such as polyethylene, polypropylene, and polyvinylidene chloride, chemical fertilizers such as ammonium sulfate, ammonium phosphate, ammonium nitrate, urea, and ammonium chloride, compost and the like can be mentioned; these are used alone or in the form of a mixture of two or more kinds.

A material that can serve as a liquid medium is selected from among those having solvency by themselves, and those not having solvency, but capable of dispersing the active ingredient compound with the aid of an auxiliary agent; representative examples include the following carriers, and these are used alone or in the form of a mixture of two or more kinds; for example, water, alcohols (for example, methanol, ethanol, isopropanol, butanol, ethylene glycol and the like), ketones (for example, acetone, methyl ethyl ketone, methyl isobutyl ketone, diisobutyl ketone, cyclohexanone and the like), ethers (for example, ethyl ether, dioxane, cellosolve, dipropyl ether, tetrahydrofuran and the like), aliphatic hydrocarbons (for example, kerosene, mineral oils and the like), aromatic hydrocarbons (for example, benzene, toluene, xylene, solvent naphtha, alkylnaphthalene and the like), halogenated hydrocarbons (for example, dichloroethane, chloroform, carbon tetrachloride, chlorinated benzene and the like), esters (for example, ethyl acetate, diisopropyl phthalate, dibutyl phthalate, dioctyl phthalate and the like), amides (for example, dimethylformamide, diethylformamide, dimethylacetamide and the like), nitriles (for example, acetonitrile and the like), dimethyl sulfoxides and the like can be mentioned.

As other auxiliary agents, the representative auxiliary agents shown as examples below can be mentioned; these auxiliary agents are used according to the intended use thereof, alone or, in some cases, in combination of two or more kinds thereof; in some cases, absolutely no auxiliary agents may be used at all.

A surfactant is used for the purpose of emulsification, dispersion, solubilization and/or wetting of active ingredient compound; for example, surfactants such as polyoxyethylene alkyl ethers, polyoxyethylene alkyl aryl ethers, polyoxyethylene higher fatty acid esters, polyoxyethylene resin acid esters, polyoxyethylenesorbitan monolaurate, polyoxyethylenesorbitan monooleate, alkyl arylsulfonates, naphthalenesulfonic acid condensation products, ligninsulfonates, and higher alcohol sulfuric acid esters can be mentioned.

For the purpose of dispersion stabilization, cohesion and/or binding of active ingredient compound, the auxiliary agents shown as examples below can also be used; for example, auxiliary agents such as casein, gelatin, starch, methylcellulose, carboxymethylcellulose, gum arabic, polyvinyl alcohol, turpentine, bran oil, bentonite, and ligninsulfonates can also be used.

The auxiliary agents shown below can be used to improve the fluidity of solid products; for example, auxiliary agents such as waxes, stearates, and phosphoric acid alkyl esters can be used. As examples of deflocculants for suspended products, auxiliary agents such as naphthalenesulfonate condensation products and condensed phosphates can also be used. As examples of antifoaming agents, auxiliary agents such as silicone oil can also be used. As antiseptics, 1,2-benzisothiazolin-3-one, para-chlorometaxylenol, butyl para-oxybenzoate and the like can also be added. Furthermore, functional spreaders, activity enhancers such as metabolic degradation inhibitors such as piperonyl butoxide, antifreezing agents such as propylene glycol, antioxidants such as BHT (dibutyl hydroxytoluene), and other additives such as ultraviolet absorbents can also be added as necessary.

The blending ratio of active ingredient can be adjusted as necessary; the active ingredient may be used in amounts chosen as appropriate over the range of 0.01 to 90 parts by weight per 100 parts by weight of nematocide; for example, when the nematocide is prepared as an emulsion, wettable powder, dust or granules, the blending ratio is suitably 0.01 to 50% by weight. A nematocide of the present invention may be used to control various nematodes as it is, or after being appropriately diluted or suspended in water and the like. The application amount of a nematocide of the present invention varies depending on various factors, for example, intended use, nematodes to be controlled, crop growth status, trend for damage occurrence, weather, environmental conditions, formulation, method of application, place of application place, timing of application and the like; the application amount may be chosen as appropriate over the range of 0.001 g to 10 kg, preferably 0.01 g to 1 kg, per 10 acres, based on an active ingredient compound.

A nematocide used in a method of the present invention may be used to control various nematodes as it is, or after being appropriately diluted or suspended in water and the like, by applying an effective amount for control of various nematodes to a subject plant in which the occurrence of the nematode is anticipated, seeds thereof or a cultivation carrier for sowing the seeds and the like according to an ordinary method; the nematocide can be used by methods of application such as application to rice nursery boxes, seed dressing, seed disinfection, planting pit treatment, plant foot treatment, planting row treatment, and soil incorporation; for various nematodes that occur in upland cropping of fruit trees, cereals, vegetables and the like, the nematocide can be applied by seed treatments such as dressing and dipping, by seedling root dipping treatment, or by soil injection, surface spraying, incorporation treatment and the like to planting row at seed sowing and the like, raising seedlings carriers such as cultivation containers for raising seedlings, planting pit, plant foots and the like, followed by watering and the like to allow the nematocide to be absorbed in the plant. The nematocide can also be applied to a water culture medium in hydroponic culture.

Seed treatment can be achieved by ordinary methods; for example, a method wherein seeds are dipped in a liquid or solid formulation, in a liquid state with or without being diluted, to allow the agent to penetrate, a method wherein a solid formulation or liquid formulation is allowed to adhere to seed surfaces by admixing with seeds, dressing treatment and the like, a method wherein a formulation is admixed with a highly adhesive carrier such as a resin or polymer, and coated over seeds in a single layer or multiple layers, a method wherein a formulation is spread around seeds simultaneously with their sowing, and the like can be mentioned. "Seed" to undergo the seed treatment, in the broader sense, has the same definition as that for "a plant body for propagation" in the present invention, and is understood to include, in addition to what are called seeds, plant bodies for vegetative propagation such as bulbs, tubers, seed potato, scaly bulbs, and stems for cuttings.

"Soil" or "cultivation carrier" as used in embodying a method of the present invention refers to a support for cultivating a plant, and the material therefor is not particularly limited, as far as the plant can grow therein; for example, what are called various soils, nursery mats, water and the like are included, and sand, vermiculite, cotton, paper, diatomaceous earth, agar, gel substances, polymeric substances, rock wool, glass wool, wood chips, barks, pumice and the like can also be included.

As examples of methods of soil application, a method wherein a liquid or solid formulation, with or without being diluted in water, is applied in the vicinity of a place where the plant is placed or a nursery bed for raising seedlings and the like, a method wherein granules are spread in the vicinity of a place where the plant is placed or a nursery bed, a method wherein a dustable powder, wettable powder, water dispersible granule, granules and the like are spread before seed sowing or before transplantation, and incorporated with the entire soil, a method wherein a dust, wettable powder, water dispersible granule, granules and the like are spread to planting pit, planting row and the like before seed sowing or setting a plant and the like can be mentioned.

For methods of paddy rice nursery box application, a nematocide of the present invention may be applied in the form of formulations such as dust, water dispersible granule, and granules, although the choice of formulation is variable depending on the time of application, for example, seed sowing period, greening period, transplanting period and the like. A nematocide of the present invention can also be applied by incorporation in ridging soil; a dust, water dispersible granule or granules and the like may be incorporated in ridging soil by, for example, bed soil incorporation, cover soil incorporation, entire ridging soil incorporation and the like. Simply, ridging soil and various formulations may be applied in alternating layers. The time of application may be before, the same, or after seed sowing, and application may take place after covering with soil.

For field crops, for example, potato, sweet potato, and soybean, preference is given to treatment of seeds or a cultivation carrier near the plant and the like in seed sowing and seedling rearing periods. For plants whose seeds are sown directly to fields, in addition to direct application to seeds, treatment of a cultivation carrier and the like near the plant being cultivated is suitable. Spreading treatment with granules, soil injection treatment with an agent in a liquid state with or without being diluted in water and the like are possible.

For treatments of cultivated plants to be transplanted in seed sowing and raising seedling periods, in addition to direct application to seeds, soil injection of a liquid agent to a nursery bed for raising seedlings or granules application is applicable. It is also possible to apply granules to planting pit at the time of planting, and to incorporate them in a cultivation carrier in the vicinity of a place of transplantation.

A nematocide of the present invention can also be used in mixture with other agents such as fungicides, insecticides, miticides, nematocides, and biotic pesticides to further expand the coverage of diseases and pests being the targets of control and the suitable period of control, or to reduce the application amount, and can also be used in mixture with herbicides, plant growth regulators, fertilizers and the like according to the situation where the nematocide is used.

Fungicides useful for these purposes include, for example, sulfur, lime sulfur, basic copper sulfate, iprobenfos, edifenphos, tolclofos-methyl, thiram, polycarbamate, Zineb, manzeb, mancozeb, propineb, thiophanate, thiophanate-methyl, benomyl, iminoctadine acetate, iminoctadine albesilate, mepronil, flutolanil, pencycuron, furametpyr, thifluzamide, metalaxyl, oxadixyl, carpropamid, dichlofluanid, flusulfamide, chlorothalonil, kresoxim-methyl, fenoxanil, hymexazol, echlomezole, fluoroimide, procymidone, vinclozolin, iprodione, triadimefon, bitertanol, triflumizole, ipconazole, fluconazole, propiconazole, difenoconazole, myclobutanil, tetraconazole, hexaconazole, tebuconazole, tiadinil, imibenconazole, prochloraz, pefurazoate, cyproconazole, isoprothiolane, fenarimol, pyrimethanil, mepanipyrim, pyrifenox, fluazinam, trifolin, diclomezine, azoxystrobin, thiadiazine, captan, probenazole, acibenzolar-S methyl, fthalide, tricyclazole, pyroquilon, quinomethionate, oxolinic acid, dithianone, kasugamycin, validamycin, polyoxin, blasticidin, streptomycin and the like;

insecticides, miticides, and nematocides useful for the same purposes include, for example, ethion, trichlorphon, methamidophos, acephate, dichlorvos, mevinphos, monocrotophos, malathion, dimethoate, formothion, mecarbam, vamidothion, thiometon, disulfoton, oxydeprofos, naled, methyl parathion, fenitrothion, cyanophos, propaphos, fenthion, prothiofos, profenofos, isophenphos, temephos, phenthoate, imethylvinphos, chlorfenvinphos, tetrachlorvinphos, phoxim, isoxathion, pyraclofos, methidathion, chlorpyrifos, chlorpyrifos-methyl, pyridafenthion, diazinon, pirimiphos-methyl, phosalone, phosmet, dioxabenzophos, quinalphos, terbufos, ethoprophos, cadusafos, mesulphenphos, DPS (NK-0795), phosphocarb, fenamiphos, isoamidofos, fosthiazate, isazophos, ethoprophos, fenthion, fosthietan, dichlofenthion, thionazin, sulprofos, fensulfothion, diamidafos, pyrethrin, allethrin, prallethrin, resmethrin, permethrin, tefluthrin, bifenthrin, fenpropathrin, cypermethrin, alfa cypermethrin, cyhalothrin, lambda cyhalothrin, deltamethrin, acrinathrin, fenvalerate, esfenvalerate, cycloprothrin, etofenprox, halfenprox, silafluofen, flucythrinate, fluvalinate, methomyl, oxamyl, thiodicarb, aldicarb, alanycarb, cartap, metolcarb, xylicarb, propoxur, fenoxycarb, fenobucarb, thiofencarb, fenothiocarb, bifenazate, BPMC (2-secondary butylphenyl-N-methylcarbamate), carbaryl, pirimicarb, carbofuran, carbosulfan, furathiocarb, benfuracarb, aldoxycarb, diafenthiuron, diflubenzuron, teflubenzuron, hexaflumuron, novaluron, lufenuron, flufenoxuron, chlorofluazuron, fenbutatin oxide, tricyclohexyltin hydroxide, sodium oleate, potassium oleate, methoprene, hydroprene, binapacryl, amitraz, dicofol, kelthane, chlorobenzilate, phenisobromolate, tetradifon, bensultap, benzomate, tebufenozide, methoxyfenozide, pyridalyl, metaflumizone, flubendiamide, chromafenozide, propargite, acequinocyl, endosulfan, diofenolan, chlorofenapyr, fenpyroximate, tolfenpyrad, fipronil, tebufenpyrad, triazamate, etoxazole, hexythiazox, nicotin sulfate, nitenpyram, acetamiprid, thiacloprid, imidacloprid, thiamethoxam, clothianidin, dinotefuran, fluazinam, pyriproxyfen, hydramethylnon, pyrimidifen, pyridaben, cyromazine, TPIC (tripropyl isocyanurate), pymetrozine, clofentezine, buprofezin, thiocyclam, fenazaquin, quinomethionate, indoxacarb, polynactin complex, milbemectin, abamectin, emamectin benzoate, spinosad, BT (*Bacillus thuringiensis*), azadirachtin, rotenone, hydroxypropyl starch, levamisole hydrochloride, metham sodium, morantel tartrate, dazomet, trichlamide, *Pasteuria penetrans, Monacrosporium phymatopagam* and the like; herbicides useful for the same purposes include, for example, glyphosate, sulfosate, glufosinate, bialaphos, butamifos, esprocarb, prosulfocarb, benthiocarb, pyributycarb, asulam, linuron, dymron, isouron, bensulfuron-methyl, cyclosulfamuron, cinosulfuron, pyrazosulfuron-ethyl, azimsulfuron, imazosulfuron, thenylchlor, alachlor, pretilachlor, clomeprop, etobenzanid, mefenacet, pendimethalin, bifenox, acifluorfen, lactofen, cihalofop-butyl, ioxynil, bromobutide, alloxydim, sethoxydim, napropamide, indanofan, pyrazolate, benzofenap, pyraflufen-ethyl, imazapyr, sulfentrazone, cafenstrole, pentoxazone, oxadiazon, paraquat, diquat, pyriminobac, simazine, atrazine, dimethametryn, triaziflam, benfuresate, fluthiacet-methyl, quizalofop-ethyl, bentazone, calcium peroxide and the like.

EXAMPLES

The present invention is hereinafter described specifically with reference to the following Examples, to which, however, the present invention is not limited unless deviating from the gist of the invention. Given below are representative preparation examples and test examples of the present invention, which are not to limit the invention.

In the Preparation Examples, part(s) indicate part(s) by weight.

Preparation Example 1

| Each compound listed in Table 1 | 10 parts |
| Xylene | 70 parts |
| N-methylpyrrolidone | 10 parts |
| Mixture of polyoxyethylene nonylphenyl ether and calcium alkylbenzenesulfonate | 10 parts |

These ingredients were uniformly blended and dissolved to obtain an emulsion.

Preparation Example 2

| Each compound listed in Table 1 | 3 parts |
| Clay powder | 82 parts |
| Diatomaceous earth powder | 15 parts |

These ingredients were uniformly blended and milled to obtain a dust.

Preparation Example 3

| Each compound listed in Table 1 | 5 parts |
| Mixed powder of bentonite and clay | 90 parts |
| Calcium ligninsulfonate | 5 parts |

These ingredients were uniformly blended, kneaded with the addition of an appropriate amount of water, granulated, and dried, to obtain granules.

Preparation Example 4

| Each compound listed in Table 1 | 20 parts |
| Kaolin and synthetic highly-dispersed silicic acid | 75 parts |
| Mixture of polyoxyethylene nonylphenyl ether and calcium alkylbenzenesulfonate | 5 parts |

These ingredients were uniformly blended and milled to obtain a wettable powder.

The utility of a nematocide of the present invention is now demonstrated by means of Test Examples. The compounds are identified by the compound numbers shown in Table 1.

Test Example 1

Nematocidal Test on the Southern Root-Knot Nematode (*Meloidogyne incognita*)

An emulsion comprising each compound listed in Table 1 as an active ingredient was prepared as directed in Preparation Example 1, and diluted to obtain active ingredient concentrations of 300 ppm and 30 ppm. Each of these dilutions (1 ml) was applied to the foots of pot-grown melon seedlings by injection; 1 day after application of the dilution, an aqueous suspension of southern root-knot nematodes (about 500 nematodes/ml) was inoculated (soil injection), to a treated plot and an untreated plot and the pots were placed in a 25° C. greenhouse. Eight days after the inoculation, the roots were washed with water and examined for the number of root knots, and the effects were determined according to the following rating criteria.

[Rating Criteria]
A: no root knots.
B: root knots are present but their number is definitely smaller than that for untreated plot.
C: root knots are present in an equivalent number to or a larger number than that for untreated plot.

As a result of the above-described test, the compounds listed in Table 1 exhibited good activity with the rating A at 300 ppm; particularly, Compound Numbers 3, 7 and 12 exhibited good activity with the rating A even at 30 ppm.

Test Example 2

Nematocidal Test on the Soybean Cyst Nematode (*Heterodera grycines*)

A wettable powder comprising each compound listed in Table 1 as an active ingredient was prepared as directed in Preparation Example 4, and 75 mg and 7.5 mg were weighed out so that the active ingredient content would be 15 mg and 1.5 mg per kg soil; these agents were mixed in soil (1000 g) contaminated with soybean cyst nematodes in a plastic bag. The treated soil was filled in pots, soybean seeds were sown, and the pots were placed in a glass greenhouse. Forty days after the seeding, the soil on the roots was put down, the number of cysts was examined, and the effect was determined according to the rating criteria shown below.

[Rating Criteria]

A: no cysts.

B: cysts are present but their number is definitely smaller than that for untreated plot.

C: cysts are present in an equivalent number to or a larger number than that for untreated plot.

As a result of the above-described test, the compounds listed in Table 1 exhibited good activity with the rating A at 75 mg; particularly, Compound Number 7 exhibited good activity with the rating A even at 7.5 mg.

INDUSTRIAL APPLICABILITY

The nematocide of the present invention exerts a reduced impact on the global environment, exhibits a broad nematode control spectrum at low application rates, and is useful as a nematocide having an excellent nematode control effect.

This application is based on a patent application No. 2007-104494 filed in Japan, the contents of which are incorporated in full herein by this reference.

The invention claimed is:

1. A method of controlling nematodes, comprising applying an effective amount of an N-2-(pyridyl)ethylcarboxamide derivative represented by the formula (I):

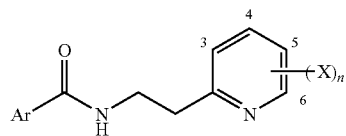

wherein,
Ar is a substituted phenyl group having one or more, the same or different substituents selected from a halogen atom, a $(C_1-C_6)$ alkyl group, a halo$(C_1-C_6)$ alkyl group, a $(C_1-C_6)$ alkylthio group, a halo$(C_1-C_6)$ alkylthio group, a $(C_1-C_6)$ alkoxy group and a halo$(C_1-C_6)$ alkoxy group; or a substituted pyrazolyl group having one or more, the same or different substituents selected from a halogen atom, a $(C_1-C_6)$ alkyl group, a halo$(C_1-C_6)$ alkyl group, a $(C_1-C_6)$ alkylthio group, a halo$(C_1-C_6)$ alkylthio group, a $(C_1-C_6)$ alkoxy group and a halo$(C_1-C_6)$ alkoxy group;
X may be the same or different, and is a halogen atom, a $(C_1-C_6)$ alkyl group, a halo$(C_1-C_6)$ alkyl group, a $(C_1-C_6)$ alkoxy group or a halo$(C_1-C_6)$ alkoxy group, and
n is the integer 0 to 4, or a salt thereof to a subject crop plant, subject crop plant seeds, or soil used to cultivate the plant.

2. The method of claim 1, wherein Ar is a substituted phenyl group having one or more, the same or different substituents selected from a halogen atom, a $(C_1-C_6)$ alkyl group, a halo$(C_1-C_6)$ alkyl group and a $(C_1-C_6)$ alkylthio group; or a substituted pyrazolyl group having one or more, the same or different substituents selected from a halogen atom and a $(C_1-C_6)$ alkyl group; X may be the same or different, and is a halogen atom or a halo$(C_1-C_6)$ alkyl group; and n is the integer 0 to 3.

3. The method of claim 1, wherein the N-2-(pyridyl)ethylcarboxamide derivative is N-[2-(3-chloro-5-trifluoromethylpyridin-2-yl)ethyl]-2-trifluoromethylbenzamide or a salt thereof.

* * * * *